United States Patent
Meyer-Böhm et al.

(10) Patent No.: US 9,439,971 B2
(45) Date of Patent: Sep. 13, 2016

(54) USE OF POLYETHER-BASED AND VINYL MONOMER-BASED COPOLYMERS AS BINDERS FOR DOSING FORMS COMPRISING SOLID ACTIVE INGREDIENTS

(71) Applicant: BASF SE, Ludwigshafen (DE)

(72) Inventors: Kathrin Meyer-Böhm, Feucht (DE); Rainer Dobrawa, Stuttgart (DE); Angelika Maschke, Mannheim (DE); Karl Kolter, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 145 days.

(21) Appl. No.: 13/732,833

(22) Filed: Jan. 2, 2013

(65) Prior Publication Data

US 2013/0123373 A1    May 16, 2013

Related U.S. Application Data

(62) Division of application No. 13/120,598, filed as application No. PCT/EP2009/062199 on Sep. 21, 2009, now abandoned.

(30) Foreign Application Priority Data

Sep. 25, 2008 (EP) .................... 08165113

(51) Int. Cl.
   *A61K 9/16* (2006.01)
   *A61K 47/34* (2006.01)
   *A61K 47/32* (2006.01)
   *A61K 9/20* (2006.01)

(52) U.S. Cl.
   CPC ............ *A61K 47/34* (2013.01); *A61K 9/1641* (2013.01); *A61K 9/2031* (2013.01); *A61K 9/2095* (2013.01)

(58) Field of Classification Search
   CPC ............ A61K 9/1641; A61K 9/2095; A61K 9/2031; A61K 47/34; C08F 283/06; C08G 64/183; C08G 2/38; C08G 18/632
   USPC ........................... 514/772.7, 772.5; 424/489
   See application file for complete search history.

(56) References Cited

U.S. PATENT DOCUMENTS

| | | | |
|---|---|---|---|
| 3,767,587 A | 10/1973 | Claussen et al. | |
| 4,728,642 A * | 3/1988 | Pawelchak et al. | 514/57 |
| 6,066,334 A * | 5/2000 | Kolter et al. | 424/465 |
| 6,534,090 B2 * | 3/2003 | Puthli | A61K 9/0004 424/469 |
| 7,413,750 B2 * | 8/2008 | Kolter | A61K 9/1635 424/469 |
| 7,629,425 B2 | 12/2009 | Dobrawa et al. | |
| 8,632,763 B2 * | 1/2014 | Bouillo et al. | 424/78.17 |
| 2002/0012701 A1 * | 1/2002 | Kolter | A61K 9/1635 424/468 |
| 2002/0015730 A1 * | 2/2002 | Hoffmann et al. | 424/470 |
| 2008/0293828 A1 * | 11/2008 | Bouillo et al. | 514/772.3 |
| 2010/0047203 A1 | 2/2010 | Dieckmann et al. | |
| 2010/0204425 A1 | 8/2010 | Mertoglu et al. | |
| 2011/0178183 A1 | 7/2011 | Meyer-Boehm et al. | |

FOREIGN PATENT DOCUMENTS

| | | |
|---|---|---|
| DE | 2016470 | 4/1970 |
| DE | 19844903 | 4/2000 |
| EP | 2158922 | 3/2010 |
| WO | WO-2007/051743 | 5/2007 |
| WO | WO-2008/058848 | 5/2008 |
| WO | WO-2008/080773 | 7/2008 |
| WO | WO-2009/013202 | 1/2009 |
| WO | WO-2010/034688 | 4/2010 |

OTHER PUBLICATIONS

Toussey (The Granulation Process 101, Basic Technologies for Tablet Making, Pharmaceutical Technology, Tableting & Granulation (2002) pp. 8-13), 6 pages.*
Britannica Online Encyclopedia, Solid Solution, [Retrieved from internet <URL: http://www.britannica.com/science/solid-solution ], [Downloaded Oct. 8, 2015], 1 page.*
Briens et al., Monitoring Fluidized Bed Drying of Pharmaceutical Granules, AAPS, Pharm Sci Tech, vol. 11, No. 4 (Dec. 2010), DOI: 10.1208/s12249-010-9538-1; pp. 1612-1618.*
Britannica Online Encyclopedia, Solid Solution [Retrieved from internet <URL: http://www.britannica.com/print/article/553329 >], [Downloaded Oct. 8, 2015], 1 page.*
Challener, Granulation Method and Process Monitoring Matter, PharmaTech.com, Advancing Development and Manufacturing (Sep. 25, 2013), [Retrieved from internet <URL: http://www.pharmtech.com/print/203118?page=full >], 2 pages.*
Kennedy, Properties of block versus random copolymers, Polymer Engineering & Science, vol. 8, issue 3, pp. 216-226 (Jul. 1968) (Abs. and citation information provided), 2 pages.*
Remington's Pharmaceutical Sciences, 17th Ed. (1985) (Gennaro, Editor), Chapter 90, Oral Solid Dosage Forms, pp. 1603-1632 (39 pages total).*

(Continued)

*Primary Examiner* — Anna Pagonakis
*Assistant Examiner* — Miriam A Levin
(74) *Attorney, Agent, or Firm* — Marshall, Gerstein & Borun LLP

(57) ABSTRACT

The use of water-soluble or water-dispersible copolymers which are obtained by free radical-initiated polymerization of a mixture of i) 30 to 80% by weight N-vinyllactam, ii) 10 to 50% by weight vinylacetate and iii) 10 to 50% by weight of a polyether, with the proviso that the total of i), ii) and iii) is equal to 100% by weight, as binders for producing solid active ingredient-containing dosage forms.

7 Claims, No Drawings

(56) References Cited

OTHER PUBLICATIONS

Kennedy, Properties of Block versus Random Copolymers, Polymer Engineering and Science, (Jul. 1968), vol. 8, No. 3, pp. 216-226.*

IPRP and Written Opinion in PCT/EP2009/062199, dated Apr. 19, 2011, 8 pgs.
Tousey, Michael D., "The Granulation Process 101 Basic Technologies for Tablet Making", *Pharmaceutical Technology* 2002, 5 pgs.

* cited by examiner

USE OF POLYETHER-BASED AND VINYL MONOMER-BASED COPOLYMERS AS BINDERS FOR DOSING FORMS COMPRISING SOLID ACTIVE INGREDIENTS

CROSS-REFERENCE TO RELATED APPLICATION

This application is a divisional of U.S. patent application Ser. No. 13/120,598, filed Mar. 23, 2011, which is a 371 of International Application Ser. No. PCT/EP2009/062199 filed Sep. 21, 2009, which claims the benefit of European Application Ser. No. 08165113.5 filed Sep. 25, 2008, all of which are incorporated herein by reference in their entireties.

DESCRIPTION

The present invention relates to the use of copolymers which are obtained by polymerizing vinyl acetate and N-vinyllactams in the presence of a polyether as binders, especially as dry binders, for solid active ingredient-containing dosage forms, especially tablets.

Binders improve the compressibility of active ingredient-containing formulations to solid dosage forms by improving the particle adhesion.

Criteria for the standard of quality when testing compressed dosage forms such as tablets are according to the European Pharmacopoeia the uniformity of mass (weight uniformity), resistance to crushing, friability and disintegration.

Cellulose powders, for example microcrystalline or microfine celluloses, result in very hard tablets, but adversely affect the flowability of the mixture for tableting.

Further binders such as hydroxypropylmethylcelluloses or polyvinylpyrrolidones are very effective wet binders.

Dry binders suitable for granulation without addition of solvents or direct compression are hydroxypropylcelluloses or copovidone (copolymer of N-vinylpyrrolidone and vinyl acetate in the ratio 60:40 by weight).

The previously disclosed binders, especially those suitable as dry binders, are frequently able to satisfy the various criteria for the standards of quality only in part. Thus, tablet strength and disintegration time often show antipodal behavior. The friability, that is the attrition, may also be unsatisfactorily high both for soft tablets through edge attrition and for very hard tablets through capping tendencies.

The object therefore was to provide novel and improved binders, especially dry binders, for pharmaceutical, cosmetic, food product, agrotechnical or other industrial applications which show improved properties in terms of the resistance to crushing and friability of the dosage forms.

WO 2007/051743 discloses the use of copolymers obtained by polymerizing N-vinyllactam, vinyl acetate and polyethers as solubilizers for active ingredients which are slightly soluble in water.

The object has been achieved according to the invention by the use of water-soluble or water-dispersible copolymers which are obtained by free radical-initiated polymerization of a mixture of
  i) 30 to 80% by weight of N-vinyllactam,
  ii) 10 to 50% by weight of vinyl acetate and
  iii) 10 to 50% by weight of a polyether,
with the proviso that the total of i), ii) and iii) is equal to 100% by weight, as binders for producing solid active ingredient-containing dosage forms.

Preferred polymers are obtained from:
  i) 30 to 70% by weight of N-vinyllactam
  ii) 15 to 35% by weight of vinyl acetate, and
  iii) 10 to 35% by weight of a polyether.

Particularly preferred polymers are obtained from:
  i) 40 to 60% by weight of N-vinyllactam
  ii) 15 to 35% by weight of vinyl acetate
  iii) 10 to 30% by weight of a polyether.

The proviso that the total of components i), ii), and iii) equals 100% by weight also applies to the preferred and particularly preferred compositions.

Suitable as N-vinyllactam are N-vinylcaprolactam or N-vinylpyrrolidone or mixtures thereof. N-Vinylcaprolactam is preferably used.

Suitable polyethers are preferably polyalkylene glycols. The polyalkylene glycols may have molecular weights of from 1000 to 100 000 D [daltons], preferably 1500 to 35 000 D, particularly preferably 1500 to 10 000 D. The molecular weights are determined on the basis of the OH value measured as specified in DIN 53240.

Suitable polyalkylene glycols which are particularly preferred are polyethylene glycols. Also suitable are polypropylene glycols, polytetrahydrofurans or polybutylene glycols, which are obtained from 2-ethyloxirane or 2,3-dimethyloxirane.

Suitable polyethers are also random or block copolymers of polyalkylene glycols obtained from ethylene oxide, propylene oxide and butylene oxides, such as, for example, polyethylene glycol-polypropylene glycol block copolymers. The block copolymers may be of the AB or ABA type.

The preferred polyalkylene glycols also include those alkylated on one or both terminal OH groups. Suitable alkyl radicals are branched or unbranched $C_1$- to $C_{22}$-alkyl radicals, preferably $C_1$-$C_{18}$-alkyl radicals, for example methyl, ethyl, n-butyl, isobutyl, pentyl, hexyl, octyl, nonyl, decyl, dodecyl, tridecyl or octadecyl radicals.

General processes for preparing the copolymers of the invention are known per se. The preparation takes place by free radical-initiated polymerization, preferably solution polymerization, in nonaqueous, organic solvents or in mixed nonaqueous/aqueous solvents. The preparation of the copolymers and their conversion into the powder form is described in detail in WO 2007/051743, the disclosure of which concerning the preparation of the copolymers is hereby incorporated by reference.

The polymers have Fikentscher K values in the range from 10 to 60, preferably 15 to 40, measured in a 1% by weight ethanolic solution.

The polymers are suitable according to the invention as binders for producing solid dosage forms, especially as binders for producing tablets.

The polymers have glass transition temperatures in the range from 30 to 120° C., preferably from 50 to 80° C.

The use as dry binders for powder mixtures for direct tableting is preferred.

The polymers are, however, also suitable for use in wet granulation, fluidized-bed granulation or dry granulation.

In the case of wet granulation, the binder may be employed in the form of an aqueous or else organic solution comprising preferably 1 to 30% by weight of binder. The polymer solution may be granulated with the other ingredients in, for example, a mixer or kneading device.

In the case of fluidized-bed granulation, the binder in the form of a solution, preferably an aqueous solution, may be sprayed onto a fluid bed of components in powder form, and agglomeration takes place. Located within the fluid bed there may be the active pharmaceutical ingredients and/or further pharmaceutical excipients.

According to one other preferred embodiment, the polymers are also suitable for processing by sinter granulation. In this case the polymers are softened by the energy input from the mixing operation, and/or as a result of elevated temperature, and as a result of this softening there is agglomeration of the components employed. As a result of the softening and subsequent solidification by cooling, solid-material bridges are formed. The operation may be conducted such that there is surface softening or partial softening of the polymer particles. It is also possible to operate the sinter granulation in such a way that there is complete softening of the polymers. Complete softening may be advisable if particularly strong binder bridges are desired.

Sinter granulation may take place in a heatable mixer, kneading device or screw extruder.

In the case of processing in a screw extruder, the extruder is used without a die plate, in other words in open mode. The process takes place without pressure being applied. Through a suitable choice of screw configuration it is possible to set the particle size of the granules with a narrow particle size distribution. The screw configuration to be selected for this purpose, as a function of the mixture used, can be determined by the skilled person, by means of a few suitable tests.

Sinter granulation may take place at temperatures of 50 to 120° C., preferably 70 to 100° C. The temperature particularly suitable is dependent on the composition of the mixture. Where plasticizing substances are included in the processing operation, lower temperatures may optionally be selected.

Irrespective of the granulating method used, it is possible to incorporate, for example, the active pharmaceutical ingredients and also other pharmaceutical excipients, such as surface-active compounds, further binders, fillers, acidifiers, buffers, flavors and fragrances, stabilizers or colorants into the granules.

To produce the solid dosage forms, the active pharmaceutical ingredient may be processed intragranularly or extragranularly. Thus it is possible to produce granules which comprise further pharmaceutical excipients but no active ingredient, and then to mix these granules with the active ingredients. It is also possible to incorporate an active ingredient both intragranularly and extragranularly. Combinations of the different active ingredients may also be used. In the case of active ingredients which are incompatible with one another, one may be processed intragranularly and the other extragranularly.

The granule particles may have average particle sizes of 100 to 1000 µm, preferably 200 to 600 µm. In the granule particles the fraction of binder according to the invention may be 1 to 60%, preferably 5 to 30% by weight.

The binder of the invention can be employed in amounts of from 1 to 20% by weight, preferably 1 to 10% by weight, based on the total weight of the dosage form.

Pharmaceutical preparations for producing solid dosage forms may, besides the binders of the invention, also comprise conventional pharmaceutical excipients such as fillers, disintegrants, coloring agents, flavorings, film-forming water-insoluble polymers, thickeners or surface-active agents, and further conventional binders in the amounts conventional for this purpose.

Examples of suitable fillers are sugars, sugar alcohols or mixtures thereof. Suitable sugars or sugar alcohols are trehalose, mannitol, erythritol, isomalt, maltitol, lactitol, xylitol, sorbitol. Furthermore, inorganic substances may also be used as fillers. Suitable in this case are dicalcium and tricalcium phosphates.

As disintegrants can be employed in amounts of from 1 to 25% by weight, preferably 2 to 15% by weight, particularly preferably 3 to 10% by weight. Such disintegrants are water-insoluble but not film-forming. Examples of suitable disintegrants are crospovidone, a crosslinked polymer of N-vinylpyrrolidone. Also suitable is croscarmellose, a cross-linked carboxymethylcellulose, where croscarmellose also means according to the invention the sodium and calcium salts thereof. Also suitable is sodium carboxymethyl starch. L-Hydroxypropylcellulose, preferably with 5 to 16% hydroxypropyl groups, is likewise suitable.

Further excipients which can be employed are water-insoluble polymers which are insoluble in the pH range from 1 to 14, that is have a pH-independent insolubility in water at every pH. However, also suitable are polymers which are insoluble in water at every pH in the pH range from 6 to 14, but are soluble in an acidic medium. The polymers may be film-forming polymers. Film-forming means in this connection that the polymers have a minimum film-forming temperature of from −20 to +150° C., preferably 0 to 100° C., in aqueous dispersion.

Suitable polymers are polyvinyl acetate, ethylcellulose, methyl methacrylate-ethyl acrylate copolymers, ethyl acrylate-methyl methacrylate-trimethylammoniumethyl methacrylate terpolymers, butyl methacrylate-methyl methacrylate-dimethylaminoethyl methacrylate terpolymers. The acrylate-methacrylate copolymers are described in detail in the European Pharmacopoeia as polyacrylate dispersion 30%, in the USP as ammonio methacrylate copolymer and in JPE as aminoalkyl-methacrylate copolymer E. Polyvinyl acetate can be employed as aqueous dispersion with solids contents of from 10 to 45% by weight. Additionally preferred is polyvinyl acetate with a molecular weight of between 100 000 and 1 000 000 daltons, particularly preferably between 200 000 and 800 000 daltons.

The formulations may further comprise as components additional water-soluble polymers in amounts of from 0 to 15% by weight. Suitable water-soluble polymers are for example polyvinylpyrrolidones, vinylpyrrolidone-vinyl acetate copolymers, polyvinyl alcohols, polyvinyl alcohol-polyethylene glycol graft copolymers, polyethylene glycols or ethylene glycol-propylene glycol block copolymers.

It is further possible to employ thickeners such as methylcellulose, hydroxypropyl-methylcellulose, hydroxypropylcellulose, hydroxyethylcellulose, carrageenans, pectins, xanthans or alginates. It is possible by adding thickeners such as, for example, high molecular weight polysaccharides for the mouthfeel to be additionally improved by increasing the softness and the sensation of volume.

It is possible if desired to employ further pharmaceutically customary excipients in amounts of from 0 to 15% by weight, for example such as acidifiers, buffer substances, sweeteners, flavorings, flavor enhancers and colorants. The following substances are particularly suitable in this connection: citric acid, tartaric acid, ascorbic acid, sodium dihydrogenphosphate, cyclamate, saccharin Na, aspartame, menthol, peppermint flavor, fruit flavors, vanilla flavor, glutamate, riboflavin, beta carotene, water-soluble colorants, finely divided color lakes.

In addition, surface-active compounds can also be added, for example sodium lauryl sulfate, dioctyl sulfosuccinate, alkoxylated sorbitan esters such as polysorbate 80, polyalkoxylated derivatives of castor oil or hydrogenated castor oil, for example Cremophor® RH 40, alkoxylated fatty acids, alkoxylated hydroxy fatty acids, alkoxylated fatty alcohols, alkali metal salts of fatty acids and lecithins.

It is further possible to add pigments such as iron oxides, titanium dioxide, colloidal or precipitated silica, calcium carbonates or calcium phosphates.

The finished tablets can also be provided with conventional coatings.

EXAMPLES

The angle of repose and the flow rate were determined in accordance with DIN ISO 4324. The bulk density was determined in accordance with Pharm. Eur. 5.

Apparatus used: tablet tester (Krämer), tablet disintegration tester ZT 74 (ERWEKA), friability tester TAR 20 (ERWEKA)

Example 1

Dry Binder

The binding power was assessed on a polymer A, obtained from 13% by weight polyethylene glycol PEG 6000, 57% by weight N-vinylcaprolactam and 30% by weight vinyl acetate with a K value of 35.

For comparison, the binding power of povidone K30 (polyvinylpyrrolidone of K value 30) and of copovidone (copolymer of N-vinylpyrrolidone and vinyl acetate in a weight ratio of 60:40, K value 28; Kollidon® VA 64, BASF), and of mixtures without binder, was assessed as follows.

| Assessment | good | moderate | poor |
|---|---|---|---|
| Resistance to crushing [N] | >75 | 60-75 | <60 |
| Friability [%] | <0.5 | 0.5-1.0 | >1.0 |
| Disintegration [min] | <4 | 4-6 | >6 |
| Weight uniformity [%] | <0.6 | 0.6-0.8 | >0.8 |

The following compositions were used:
per 500 mg tablet weight
200.00 mg of ascorbic acid powder
231.25 mg of Ludipress[1)]
50.00 mg of binder
15.00 mg of crospovidone[2)]
1.25 mg of colloidal silicon dioxide[3)]
2.50 mg of magnesium stearate 1) Ludipress®: formulation of 93% by weight lactose, 3.5% by weight povidone K30 (Kollidon® 30, from BASF), 3.5% by weight crospovidone
   2) Crospovidone: Kollidon® CL, from BASF
   3) Aerosil® 200, from Evonik The mixture of components was passed through a sieve with a mesh width of 0.8 mm, put in a glass bottle and mixed in a Turbula mixer for 10 minutes, and compressed to tablets.

Tablet format: 12 mm diameter, beveled
Compressive force: 18 kN
Tableting rate: 30 rpm rotary press The tablets were subsequently tested for their physical properties.

| Binder | Povidone K30 | Copovidone | No binder | Polymer A according to the invention |
|---|---|---|---|---|
| Resistance to crushing [N] | 65 | 90 | 49 | 87 |
| Friability [%] | 0.43 | 1.14 | 3.5 (15% breakage) | 0.44 |
| Disintegration [min · sec] | 1.19 | 1.02 | 0.24 | 2.30 |
| Weight uniformity [%] | 4.12 | 0.58 | 1.01 | 0.34 |

The binder used according to the invention therefore results in tablet resistances to crushing which are comparable to those of tablets comprising copovidone, but at the same time in particular results in distinctly lower friability.

Example 2

Wet Binder

| Formula | Initial mass [g] | Composition after drying [% by weight] |
|---|---|---|
| Calcium hydrogenphosphate | 350.00 | 80.8 |
| Lactose | 50.00 | 11.5 |
| Binder | 12.40 | 2.9 |
| DI water | 55.00 | — |
| Kollidon CL | 18.56 | 4.3 |
| Magnesium stearate | 2.06 | 0.5 |

Calcium hydrogenphosphate and lactose were weighed out into a Diosna mixer (Diosna P 1/6 (2 L stirring vessel)) and the mixture was mixed for 1 minute (200 rpm stirrer/ 2200 rpm chopper). An aqueous solution of binder with a strength of 18.4% by weight was added dropwise over the course of 4 minutes with continual stirring (at 200 rpm stirrer/2200 rpm dropper). Following addition of the binder solution to the mixture, mixing was continued for 2 minutes. The stirrer speed was then raised to 1500 rpm for 30 seconds, while the chopper continued to run at 2200 rpm. Thereafter the moistened mass was passed through a sieve with a mesh size of 0.8 mm, and the wet granules were dried in air on racks for 12 hours. The absolute loss of the granules on drying was determined using an IR drier to constant mass of 80° C. Subsequently Kollidon CL and magnesium stearate were added. The overall mass was passed through a sieve with a mesh size of 0.8 mm and introduced into a glass bottle, which was sealed, followed by mixing for 5 minutes in a Turbula mixer (Turbula mixer T2, Willy A Bachofen AG).

Tablets were then produced and tested as described in Example 1.

Tablet Analysis:

| Pressing pressure | Binder | Resistance to crushing [N] | Friability [%] | Disintegration [s] |
|---|---|---|---|---|
| 18 kN | Inventive, polymer A | 103 | 0.13 | 31 |
| | Kollidon VA 64 | 83 | 0.37 | 38 |
| | Kollidon 30 | 95 | 0.18 | 35 |
| | Kollidon 90 F | 109 | 0.15 | 117 |

The inventive polymer used, in comparison to known binders, had a higher binding strength in tandem with an improved friability and more rapid disintegration.

Example 3

Sintered Granules

| Formula | Composition [% by weight] |
| --- | --- |
| Polymer A | 50 |
| Lactose | 45 |
| PEG 400 | 5 |

The polymer and the lactose (Granulac® 230, average particle size 27 μm) were weighed out into a Stephan mixer (UMC 5). The product container was heated at 95° C. by means of a double-jacket design and connected oil bath. This mixture was mixed for 5 minutes (with a stirrer speed of 1000 rpm). After a homogenous mixture had been achieved, polyethylene glycol (PEG 400; Lutrol® E 400, BASF SE) was added dropwise to the mixture, and mixing was continued at the same speed for a further 20 minutes. The finished granules were subsequently passed through a sieve (mesh size 1000 μm) to remove oversize. The resultant granules were characterized and showed successful agglomeration of the lactose. The average particle diameter increased from 27 μm (Granulac 230) to 396 μm (lactose granules with polymer A).

Surprisingly, the granules formed had virtually no fine fraction, which suggests uniform agglomeration behavior. This is evidenced by the $d_{10}$ value of 228 μm, which means that less than 10% by weight of the particles have a particle size of less than 228 μm.

The bulk density of the granules was 0.63 g/ml as determined using the bulk/tamp volumeter in accordance with Ph. Eur. The flow behavior of the granules, determined by means of a Pfrengle funnel, gave an angle of repose of 26.6° and a flow time of 7.2 seconds.

The granules were subsequently compressed to form tablets. Prior to the tableting of the finished granules, 5% by weight of disintegrant (crospovidone; Kollidon® CL) and 0.5% by weight of lubricant (magnesium stearate) were added. The total mass was passed again through a sieve with a mesh size of 1.0 mm and introduced into a glass bottle, which was sealed, and mixing took place for 5 minutes in a Turbula mixer. The pressing mixture was compressed on an eccentric press (EK0 eccentric press) at 18 kN to give tablets with a size of 12 mm.

The properties of the tablets were as follows:
Resistance to crushing: 80 N
Friability: 0.2%
Disintegration: 50 s

Example 4

Sintered Granules; Percentages [% by weight]

| Formulation 1 | Formulation 2 | Formulation 3 | Formulation 4 |
| --- | --- | --- | --- |
| 50% polymer A | 50% polymer A | 50% polymer A | 40% polymer A |
| 30% lactose | 30% lactose | 25% lactose | 35% lactose |
| 20% fenofibrate | 15% itraconazole | 20% cinnarizine | 20% cinnarizine |
| — | 5% PEG 400 | PEG 5% 600 | 5% PEG 600 |

The granules will be produced in a twin-screw extruder with a screw diameter of 16 mm (L/D ratio=40) from ThermoFisher Polylab, which is operated without pressurization and with an open head. Granulation took place at a screw speed of 100 rpm with a barrel temperature (from the $2^{nd}$ barrel onward) of 80° C.

| | Formulation 1 | Formulation 2 | Formulation 3 | Formulation 4 |
| --- | --- | --- | --- | --- |
| Angle of repose | 28° | 30° | 30° | 31° |
| Flow rate | 8 sec | 7 sec | 8.1 sec | 7.5 sec |
| Bulk density | 0.6 g/ml | 0.65 g/ml | 0.55 g/ml | 0.58 g/ml |
| Average particle diameter | 350 μm | 420 μm | 342 μm | 380 μm |

We claim:
1. A process for producing a solid pharmaceutical dosage form by wet granulation, which comprises:
    forming a granular mixture by mixing, as a binder, a water-soluble or water-dispersible copolymer which is obtained by free radical-initiated polymerization of a mixture of:
    i) 30 to 80% by weight of N-vinyllactam,
    ii) 10 to 50% by weight of vinyl acetate and
    iii) 10 to 50% by weight of a polyether,
    with the proviso that the sum of i), ii) and iii) is equal to 100% by weight, with an active pharmaceutical ingredient in solid form and optionally a further pharmaceutical excipient, and
    subsequently converting the granular mixture into the solid pharmaceutical dosage form.
2. The process according to claim 1 comprising the steps of:
    forming a solution of the binder;
    adding the solution of the binder dropwise with stirring to the active pharmaceutical ingredient and the optional further pharmaceutical excipient to form a moistened mass;
    passing the moistened mass through a sieve to form wet granules;
    drying the wet granules to form the granular mixture; and
    forming the solid dosage form from the granular mixture.
3. The process according to claim 1, wherein the further pharmaceutical excipient is present and incorporated into the granular mixture.
4. The process according to claim 1, wherein the granular mixture is converted by compression into the solid pharmaceutical dosage form.
5. The process according to claim 2, wherein solution of the binder comprises the water-soluble or water-dispersible copolymer and an aqueous solvent.
6. The process according to claim 5, wherein the aqueous solvent is water.
7. The process according to claim 2, wherein solution of the binder comprises the water-soluble or water-dispersible copolymer and an organic solvent.

* * * * *